United States Patent
McClelland et al.

[11] Patent Number: 5,191,215
[45] Date of Patent: * Mar. 2, 1993

[54] APPARATUS AND METHOD FOR TRANSIENT THERMAL INFRARED SPECTROMETRY OF FLOWABLE ENCLOSED MATERIALS

[75] Inventors: John F. McClelland; Roger W. Jones, both of Ames, Iowa

[73] Assignee: Iowa State University Research Foundation, Inc., Ames, Iowa

[*] Notice: The portion of the term of this patent subsequent to Dec. 2, 2008 has been disclaimed.

[21] Appl. No.: 749,186

[22] Filed: Aug. 23, 1991

Related U.S. Application Data

[63] Continuation-in-part of Ser. No. 546,738, Jul. 2, 1990, Pat. No. 5,070,242, which is a continuation-in-part of Ser. No. 576,448, Sep. 12, 1990, Pat. No. 5,075,552, which is a continuation-in-part of Ser. No. 415,714, Oct. 2, 1989, abandoned, which is a continuation-in-part of Ser. No. 297,297, Jan. 13, 1989, abandoned.

[51] Int. Cl.$^5$ ............................................. G01N 21/71
[52] U.S. Cl. .................................. 250/341; 250/339; 250/340; 250/343
[58] Field of Search ................. 250/343, 341, 340, 339

[56] References Cited

U.S. PATENT DOCUMENTS 4,883,963 11/1989 Kemeny et al. ..................... 250/339
5,070,242 12/1991 McClelland et al. ............... 250/339
5,075,552 12/1991 McClelland et al. ............... 250/341

*Primary Examiner*—Constantine Hannaher
*Attorney, Agent, or Firm*—Antonelli, Terry, Stout & Kraus

[57] ABSTRACT

A method and apparatus for enabling analysis of a flowable material enclosed in a transport system having an infrared transparent wall portion. A temperature differential is transiently generated between a thin surface layer portion of the material and a lower or deeper portion of the material sufficient to alter the thermal infrared emission spectrum of the material from the black-body thermal infrared emission spectrum of the material, and the altered thermal infrared emission spectrum is detected through the infrared transparent portion of the transport system while the altered thermal infrared emission spectrum is sufficiently free of self-absorption by the material of emitted infrared radiation. The detection is effected prior to the temperature differential propagating into the lower or deeper portion of the material to an extent such that the altered thermal infrared emission spectrum is no longer sufficiently free of self-absorption by the material of emitted infrared radiation. By such detection, the detected altered thermal infrared emission spectrum is indicative of characteristics relating to molecular composition of the material.

26 Claims, 3 Drawing Sheets

APPARATUS AND METHOD FOR TRANSIENT THERMAL INFRARED SPECTROMETRY OF FLOWABLE ENCLOSED MATERIALS

CROSS REFERENCE TO RELATED APPLICATIONS

This application is a continuation-in-part of copending U.S. application Ser. No. 546,738, filed Jul. 2, 1990, now U.S. Pat. No. 5,070,242 which is a continuation-in-part of U.S. application Ser. No. 576,448, filed Sep. 12, 1990, now U.S. Pat. No. 5,075,552 (corresponding to PCT/US90/00122, filed Jan. 12, 1990) which is a continuation-in-part of U.S. application Ser. No. 415,714, filed Oct. 2, 1989, now abandoned, which is a continuation-in-part of U.S. application Ser. No. 297,297, filed Jan. 13, 1989, now abandoned, the disclosures of the aforementioned applications being incorporated by reference herein.

BACKGROUND OF THE INVENTION

The present invention relates to spectroscopic analysis of materials, and particularly, to non-contact, remote spectroscopic analysis of a quantity of flowable material based on transient thermal infrared emission from the material. The flowable material includes liquids, gases, melts representing normally solid materials which have been heated above the melting temperature thereof, powders and pellets and which are enclosed in a transport system such as a container, conduit or the like.

There are numerous types of analytical methods which currently are known for deriving information about materials. Spectroscopy is a well known and general method for analyzing materials. There are a number of types of spectroscopic methods which, in turn, are applicable to certain types of analyses and measurements, and which have advantages and disadvantages.

Presently, there is a need for improvements in the ability to analyze materials, especially in those cases where such analyses need to be quick, efficient, and accurate. Additionally, there is a real need for such analyses for "in-process" situations; that is, directly on-line with respect to the manufacturing or the processing of materials.

For many materials, there are a variety of generally conventional spectroscopic methods for analyzing the content and other characteristics of the materials. Some of those methods are infrared transmission, diffuse reflectance, photoacoustic, and emission spectroscopies. While generally these methods give satisfactory results, they are deficient because they require selective, and often destructive, sampling of the materials. Some materials (coal, for example) require grinding or pulverizing. The material must often be removed to a remote laboratory location where the testing and equipment requires time and resources to provide the results.

Many of the aforementioned presently used methods also lack much flexibility in their use. While some of the methods do not require destructive sampling such as grinding or pulverizing, they may not be operable for materials of greater than minimal thickness, or for materials of varying thickness. Conventional transmission or emission spectroscopies have problems because the optical density of many materials is too high to permit accurate and reliable measurement. When a thick sample is heated, the deep layers of the sample emit strongly at the preferred wavelengths and only weakly at other wavelengths. This deep-layer strong emission at preferred wavelengths, however, is greatly attenuated before leaving the sample since surface layers of the thick sample preferentially absorb those particular wavelengths and such process is termed "self-absorption". Self-absorption in optically-thick samples causes severe truncation of strong spectroscopic bands and leads to emission spectra which closely resemble black-body emission spectra representative of an optically thick material being heated to a uniform temperature and which contain little spectral structure characteristic of the material being analyzed.

Attempts have been made to solve this self-absorption problem by thinning sample materials. High-quality spectra of free-standing films and thin layers on low-emission substrates are routinely measured. However, this requires selective sampling and processing of the materials being analyzed.

For other types of spectroscopic methods such as photoacoustic and reflection spectroscopies which are less subject to optical density problems, deficiencies exist in that they are not easily performed on moving streams of materials. Thus, there is a real need in the art for an apparatus and method which has the flexibility to be used both for moving and stationary materials; and for materials which may have significant optical densities.

In the aforementioned copending applications, transient infrared spectroscopy has been applied to materials wherein a temperature gradient is created at the surface of the analyzed material so that a thin surface layer of the material is hotter or colder than the bulk of the sample material. If the surface is heated, it emits infrared light independent of the bulk of the sample material. Since the surface layer is thin, the spectrum thereof suffers less from the phenomenon of self-absorption that obscures the emission spectra of optically thick materials and can be appropriately detected to provide an indication of characteristics relating to molecular composition of the sample material. In a similar manner, if the surface is cooled, the surface layer acts as a thin transmission sample and the transmission spectrum which is detected is impressed onto the infrared light passing through the thin surface layer that is spontaneously emitted by the uncooled bulk of the material sample to provide an indication of characteristics relating to molecular composition of the sample material. However, the prior copending applications are generally related to materials which are not enclosed in a transport system such as a container, conduit, or the like.

SUMMARY OF THE INVENTION

It is therefore a principal object of the present invention to improve upon or overcome the deficiencies and problems in the art in relation to flowable enclosed material.

Another object of the present invention is to provide an apparatus and method of thermal transient infrared transmission spectroscopy which can be utilized on flowable enclosed materials.

Another object of the present invention is to provide an apparatus and method for analyzing a flowable material enclosed in a transport system such as a container or the like by transiently generating a temperature differential between a thin surface layer portion and a lower portion sufficient to alter the thermal infrared emission spectrum from the black-body thermal emission spectrum of the material by heating or cooling the thin surface layer portion and by detecting, through an infrared transparent or transmitting portion of the transport system, the altered thermal emission spectrum of the material while the altered thermal emission spectrum is sufficiently free of self-absorption by the material of emitted infrared radiation.

Another object to the present invention is to provide an apparatus and method as above described wherein the detection and the analyzation can be accomplished generally without physical contact with the material.

A further object to the present invention is to provide an apparatus and method as above described which can be done remotely from the material being analyzed.

A further object to the present invention is to provide an apparatus and method as above described which can derive the molecular composition of a material, and various physical and chemical properties of the material that are related to molecular composition.

Another object to the present invention is to provide an apparatus and method as above described which can be utilized directly on production or processing lines which handle the materials.

A still further object to the present invention is to provide an apparatus and method as above described which is non-destructive to the material being analyzed.

A further object to the present invention is to provide an apparatus and method as above described which can also be utilized to analyze either large or small samples of the materials in laboratory settings.

A still further object to the present invention is to provide an apparatus and method as above described which can be utilized with optically dense materials. A further object to the present invention is to provide an apparatus and method as above described which overcomes the spectroscopic problems caused by self-absorption of the emitted radiation from the material being analyzed.

A further object of the present invention is to provide an apparatus and method as above described which can be utilized for an unknown quantity of flowable material, on both a continuous and non-destructive basis.

Another object of the present invention is to provide an apparatus and method as above described which can be directly utilized in-process for an unknown quantity of moving material.

A further object of the present invention is to provide an apparatus and method as above described which is economical, efficient and reliable.

Another object of the present invention is to provide an apparatus and method as above described which can operate within the extreme and changing conditions of a processing environment for materials, or within a laboratory setting.

A further object of the invention is to provide an apparatus and method as above described, which can be combined with a computer system to derive information about the materials useful for processing, control, and understanding of the material.

The present invention provides an apparatus and method for nondestructively analyzing flowable materials enclosed in a transport system by infrared spectroscopy. A temperature differential is transiently generated between a thin surface layer portion of the material and a lower or deeper portion of the material sufficient to alter the thermal infrared emission spectrum of the material from the black-body thermal infrared emission spectrum of the material. That is, by heating or cooling a part of the surface of the material, a transient temperature differential is generated between the thin surface layer portion and lower or deeper portion of the material sufficient to alter the thermal infrared emission spectrum of the material from the black-body thermal infrared emission spectrum thereof. Since this temperature differential propagates to the lower portion of the material, the altered thermal infrared emission spectrum of the material is detected while the altered thermal infrared emission spectrum is sufficiently free of self-absorption by the material of emitted infrared radiation, prior to the temperature differential propagating into the lower portion of the material to an extent such that the altered thermal infrared emission spectrum is no longer sufficiently free of self-absorption by the material of emitted infrared radiation. The altered thermal infrared emission spectrum is detected through an infrared transparent or transmitting portion of the transport system such as a window of a conduit as an infrared spectrum by a spectrometer, for example, and the spectrum contains information on the molecular composition of the material. Thereafter, characteristics relating to the molecular composition of the material may be determined based upon the detected altered thermal infrared emission.

In accordance with the present invention, a heating or cooling source applies energy to a part of the surface of the material to cause transient heating or cooling of the thin surface layer of the material. In the case of heating of the thin surface layer of the material, thermal infrared emission from the thin layer is detected through the transparent portion of the transport system and is analyzed by the detector to obtain infrared absorbance spectra of the material utilizing Kirchhoff's law. In the case of cooling of the thin surface layer of the material, superpositioning of the transmission spectrum of the cooled layer on the emission of infrared radiation from the hotter lower portion of material below the cooled layer results in the altered infrared emission which is detected by a detector through the transparent portion of the transport system. Because the bulk of the material, i.e., all of the material below the cooled or chilled layer having a depth l, is at a uniform temperature, the bulk or lower portion of the material will emit a black-body spectrum characteristic of the temperature $T_H$. If the chilled surface layer is optically thin so that $l < 1/\beta$, where $\beta$ is the absorption coefficient, then the surface layer will emit a negligible amount of infrared as compared to the amount passing through it from the bulk, both because it is thin and because emission intensity is proportional to $T^4$, so that the cooled surface layer will absorb infrared from the bulk emission and altered thermal infrared emission will be detected. Thus, the cooled or chilled layer will behave in the manner of a sample of thickness, l when placed in an infrared spectrometer whose source is at temperature $T_H$ and the emission reaching the spectrometer will be a transmission spectrum of the optically thin cooled layer and will be referred to hereinafter as a "transmission spectrum".

In accordance with the present invention, the analysis and detection of the transmission spectrum or altered thermal infrared emission is accomplished by a spectrometer and detector which, in preferred embodiments, can be, for example, a cooled HgCdTe infrared detector. The detector operates so as to detect the altered thermal infrared emission spectrum of the material which has been altered from the black body thermal infrared emission spectrum of the material as a result of the generation of the temperature differential transiently in the thin surface layer portion by cooling of such thin surface layer portion while the altered thermal infrared emission spectrum is sufficiently free of self-absorption by the material of emitted infrared radiation. That is, the detection is effected prior to the temperature differential propagating through the lower or deeper portion of the material to an extent such that the altered thermal infrared emission spectrum is no longer sufficiently free of self-absorption by the material of emitted infrared radiation. By such detection, the detected altered thermal infrared emission spectrum is indicative of characteristics relating to the molecular composition of the material.

In accordance with the present invention, the detector may be controlled by a control arrangement and/or provide an output to a control arrangement including a processor having appropriate software for deriving different characteristics from the detected and selected spectra of the infrared radiation from the material. Additionally, such control arrangement or processor may include appropriate computer memory, storage, and printer or graphic components.

These and other objects, features and advantages of the present invention will become more apparent with reference to the accompanying drawings.

DESCRIPTION OF THE PREFERRED EMBODIMENTS

Figure 1:
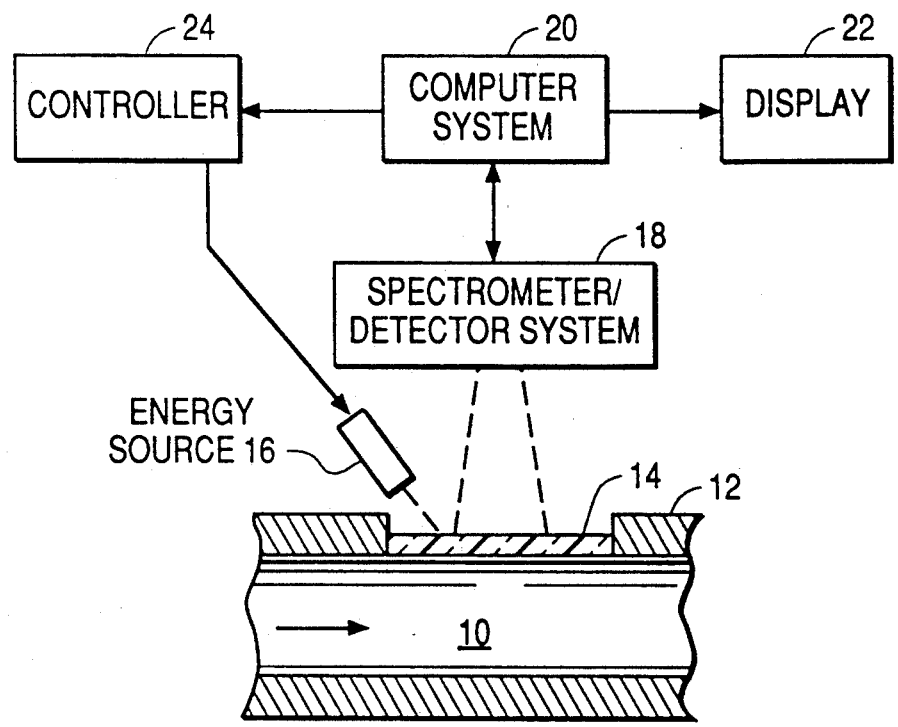
FIG. 1 is a block diagram arrangement and partial cross-sectional view of an embodiment of the present invention.

Referring now to the drawings, wherein like reference numerals are utilized to designate like parts throughout the several views, FIG. 1 illustrates an embodiment of the present invention wherein the flowable material 10 to be analyzed in the form of a liquid, a slurry or powder, flows in a transport system 12 such as a container or conduit past a thermally thin, infrared transparent or transmitting portion 14 of the transport system such as a window disposed in a wall of the container or conduit. The direction of flow of the material is indicated by the arrow. An energy source 16 applies either heating or cooling energy to the flowable material for heating or cooling the thin surface layer of the material adjacent the window. In the case of heating energy, the energy source 16 may be a hot gas jet or a laser disposed so as to apply the energy to the material through the window 14 in a pulsed or continuous manner. In the case of cooling energy, the energy source 16 may be a cooling gas jet disposed so as to apply the energy to the material through the window 14. A spectrometer/detector system 18 is disposed with respect to the window and having a field of view indicated in dashed line for observing the emission spectrum when heat energy is applied or transmission spectrum when cooling energy is applied to the thin layer through the window. Sample flow prevents the thermally altered thin surface layer which contacts the window 14 from growing so thick that its infrared opacity prevents acquisition of useful spectra.

As is known in the art, collection optics may be used to focus infrared radiation emitted by the flowable material 10 onto the spectrometer/detector system 18 and the system generates an electrical signal as a function of the wavenumber of the emitted radiation. A computer system 20 processes the signals from the system 18 in order to obtain the chemical or physical information required. The computer system 20 is coupled to a display 22 for displaying desired information including detected spectra by way of a display screen or printer, for example. The computer system may also be coupled to a controller 24 for controlling the operation of the energy and/or process parameters, for example.

Figure 2:
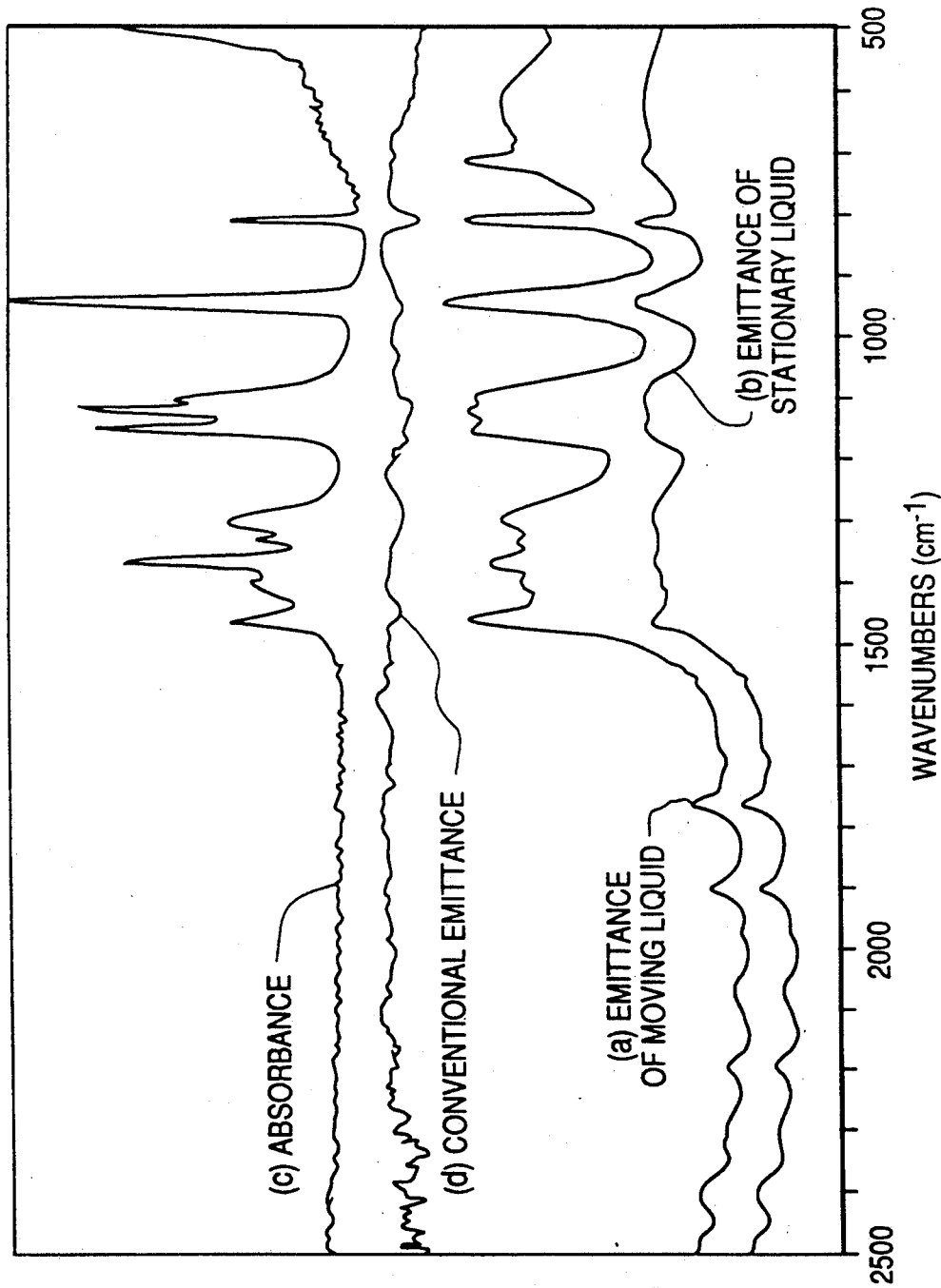
FIG. 2 is a graphical depiction of observed spectra obtained in accordance with the embodiment of FIG. 1 and conventionally obtained spectra.

FIG. 2 shows spectra of 2-propanol (ordinary rubbing alcohol) obtained in accordance with an embodiment corresponding to FIG. 1. Heat was applied utilizing a hot gas jet to the outside surface of a very thin (12 $\mu$m) window of polyethylene in the side of a container containing the 2-propanol as the liquid to be analyzed. Polyethylene has very little infrared spectrum of its own and the thinness of the window both reduced its contribution to the observed spectrum and allowed the heat applied to the outside to be readily transmitted to the liquid in the container.

The bottom two spectra (a) and (b) of FIG. 2 were taken in accordance with the embodiment of FIG. 1 wherein one spectrum (a) represents the spectrum obtained with the alcohol moving or flowing and the other spectrum (b) with the liquid in a stationary state. The top spectrum (c) is included for comparison purposes. It was taken conventionally by passing infrared light through a very thin film of the stationary alcohol; it shows the structure a spectroscopist would look for to identify the liquid. The nearly flat spectrum (d) was taken by heating up all of the alcohol in the container. The near absence in this spectrum of the structure indicative of 2-propanol is the result of self-absorption. In contrast, the bottom two spectra (a) and (b) have the same structure as the top spectrum (c), although the stronger peaks have all been truncated to approximately the same height. This too is the effect of self-absorption, but in the spectra, in accordance with the present invention, the self-absorption has been reduced to the level that analytically useful structure is present in the spectra. In the nonflowing sample, the thickness of the heated layer of alcohol that contributes to the spectrum is controlled by speeds of thermal diffusion and convection within the alcohol. When the sample is flowing, the heated layer is actively thinned by a motion much faster than convection. As a result, the spectrum of the moving liquid suffers from less self-absorption and is the better match to the absorbance spectrum at the top. The polyethylene window does contribute a small amount to the spectra in that it is responsible for the peak at 817 $cm^{-1}$ and in part for the peak at 1467 $cm^{-1}$. The rest of the structure in the detected spectra is due to the alcohol. Weak features barely visible in the top spectrum show up much more strongly in the bottom two spectra not because they are intrinsically stronger, but because the strong features are relatively much weaker due to self-absorption.

It is noted that it is difficult to provide a window as thin as the one used above in a practical application.

Figure 3:
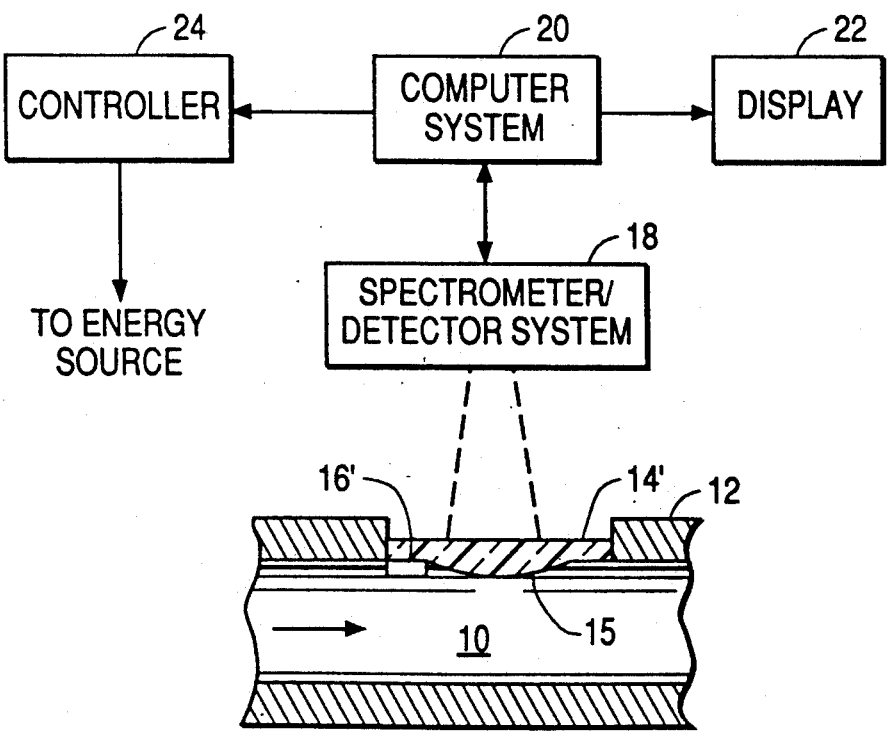
FIG. 3 is a block diagram arrangement and partial sectional view of another embodiment of the present invention.

Normally, it is expected that the window will be appreciably thicker and therefore the heat or cold source will be provided on the inside of the window. FIG. 3 shows an embodiment wherein the fluid 10 flows in the direction indicated by the arrow or past a thick infrared transparent or transmitting window 14' having a convex surface 15 protruding into the flow of the material so as to provide better contact with the material and forming a lens to assist in the gathering of the infrared signal. Heat is applied by a tantalum ribbon 16' extending perpendicular to the direction of flow at the upstream edge of the spectrometer field of view (shown by the dashed lines) of the spectrometer/detector system 18 and is held against the inner surface of the window 14' of the transport system 12. Many variations on this basic approach are of course possible. The heating element could consist of thin films deposited directly on the window within or outside the field of view of the spectrometer. Also, a heat exchanger made of small-diameter, thin-walled tubing carrying either hot or cold liquid could be attached to the window. Many other small-scale refrigerators or cooling sources (e.g., thermoelectric, Joule-Thomson) are also possible. Also, the heat or cold sources could be provided on the outside of the window rather than on the inside.

Figure 4:
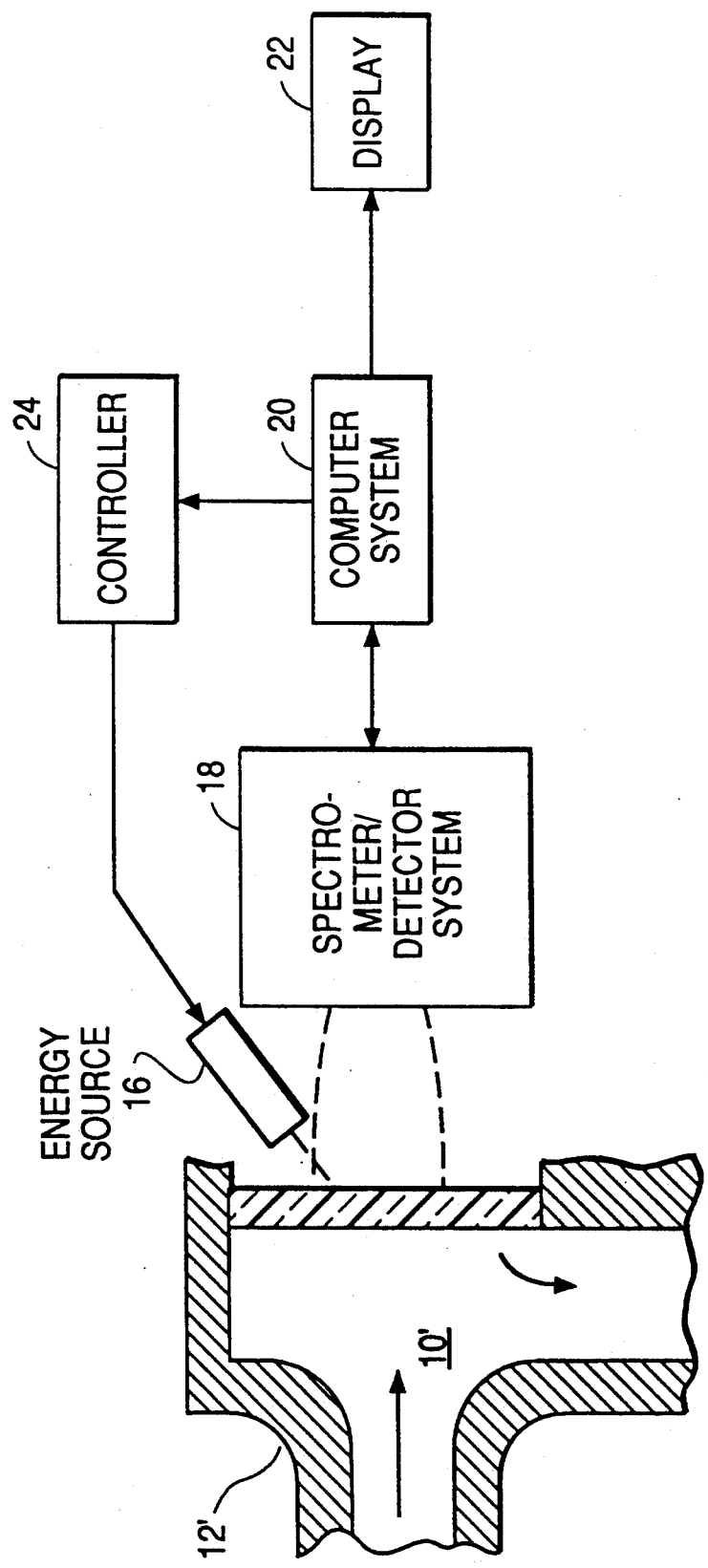
FIG. 4 is a block diagram arrangement and partial sectional view of a further embodiment of the present invention.

In cases where the material to be analyzed is made of pellets or other similar particles, it is also possible to use a heating or cooling jet. As shown in FIG. 4, pellets 10' or the like flowing in the direction of the arrows in a pneumatic transport tube 12', as is often used in industry, will have substantial momentum. At a sharp turn in such a tube, the pellets 10' are pressed against the outside wall. A window 14" is positioned as shown in FIG. 4 so that the pellets are pressed against the window and moderate jet of hot or cold gas from the energy source 16 is applied at the upstream edge of the window to generate the thermal transient. The spectrometer/detector system 18 and other system components operate in the manner described above. This arrangement is also applicable to a sample material of two-phase such as a slurry.

The heating energy source may be a laser as described in the aforementioned copending applications so long as the window of the transport system through which the infrared spectrum is detected also enables passage of the laser beam therethrough to enable heating of the material enclosed in the transport system.

The spectrometer/detector system operates in the case of flowing material to detect substantially only the transient altered thermal emission of infrared radiation passing through the field of view thereof or in the case of stationary material is controlled to detect the transient altered thermal emission of infrared radiation for a predetermined period of time, for example.

As also described in the aforementioned copending applications, the computer system enables processing of the signal detected and measured by the spectrometer/detector system to obtain molecular concentrations or other physical or chemical information through correlation techniques as required for any number of different operations such as process control, quality control, analytical chemistry, or non-destructive evaluation application. The computer system can also include appropriate computer software and complementary data for deriving different material characteristics from infrared emission spectra. Additionally, the computer system can use appropriate software, displays, complementary data and servo systems to make decisions and send and execute commands based on the infrared spectra for process control, for example.

While we have shown and described several embodiments in accordance with the present invention, it is understood that the same is not limited thereto but is susceptible of numerous changes and modifications as known to those skilled in the art and we therefore do not wish to be limited to the details shown and described herein but intend to cover all such changes and modifications as are encompassed by the scope of the appended claims.

What is claimed is:

1. A method for enabling analysis of a flowable material enclosed in a transport system, comprising the steps of:
   transiently generating a temperature differential between a thin surface layer portion of the material and a lower portion of the material sufficient to alter the thermal infrared emission spectrum of the material from the black-body thermal infrared emission spectrum of the material; and
   detecting through an infrared transparent portion of the transport system the altered thermal infrared emission spectrum of the material while the altered thermal infrared emission spectrum is sufficiently free of self-absorption by the material of emitted infrared radiation, prior to the temperature differential propagating into the lower portion of the material to an extent such that the altered thermal infrared emission spectrum is no longer sufficiently free of self-absorption by the material of emitted infrared radiation, so that the detected altered thermal infrared emission spectrum is indicative of characteristics relating to molecular composition of the material.

2. A method according to claim 1, wherein the step of transiently generating a temperature differential includes applying energy to a surface region of the material adjacent to the infrared transparent portion of the transport system sufficient to cause transient heating in the thin surface layer portion of the material so as to enable transient thermal emission of infrared radiation from the thin surface layer portion.

3. A method according to claim 1, wherein the step of transiently generating a temperature differential includes applying energy to a surface region of the material adjacent to the infrared transparent portion of the transport system sufficient to cause transient cooling of the thin surface layer portion and superposition of the transmission spectrum of the cooled layer on the emission of infrared radiation from the lower portion of the material below the cooled layer and being at a higher temperature than the cooled layer.

4. A method according to claim 1, wherein the step of detecting through the infrared transparent portion of the transport system includes detecting substantially only the transient altered thermal infrared emission spectrum which is substantially free of self-absorption by the material of emission infrared radiation.

5. A method according to claim 1, wherein the step of applying energy to a surface region of the material includes applying one of heat and cold energy, one of pulsingly and continuously to the surface region of the material adjacent to the infrared transparent portion of the transport system.

6. A method according to claim 5, wherein the step of applying energy to the surface region of the material includes one of applying energy directly to the surface region of the material and indirectly through the infrared transparent portion of the transport system, the infrared transparent portion being a thermally transparent portion enabling transmission of the applied energy therethrough.

7. A method according to claim 1, wherein the material is one of a flowing material and a stationary material.

8. A method according to claim 7, wherein the flowable material is one of a liquid, gas, powder, pellets, and a melt.

9. A method according to claim 1, wherein the transport system includes at least one of a container and conduit for the flowable material and having the infrared transparent portion disposed as a window in a wall thereof, the step of detecting including utilizing a detector having a field of view of at least a portion of the window for detecting the transient altered thermal infrared emission spectrum of the material through the window.

10. A method according to claim 9, wherein the step of detecting includes providing a portion of the window facing the flowable material with a convex surface for enabling contact with the flowable material.

11. A method according to claim 9, wherein the material is a flowing material and is positioned in the wall of the transport system so that the moving material moves in parallel to an extent of the window.

12. A method according to claim 9, wherein the material is a moving material and the window is positioned in the wall of the transport system so as to extend transversely to an initial moving direction of the moving material so that the moving material impinges on and is deflected from the window.

13. A method according to claim 1, further comprising the step of determining characteristics relating to the molecular composition of the flowable material in accordance with the detected transient altered thermal emission.

14. An apparatus for enabling analysis of a flowable material enclosed in a transport system, comprising:
an infrared transparent member provided in a wall of the transport system;
means for transiently generating a temperature differential between a thin surface layer portion of the material and a lower portion of the material sufficient to alter the thermal infrared emission spectrum of the material from the black-body thermal infrared emission spectrum of the material; and
means for detecting through the infrared transparent portion of the transport system the altered thermal infrared emission spectrum of the material while the altered thermal infrared emission spectrum is sufficiently free of self-absorption by the material of emitted infrared radiation, prior to the temperature differential propagating into the lower portion of the material to an extent such that the altered thermal infrared emission spectrum is no longer sufficiently free of self-absorption by the material of emitted infrared radiation, so that the detected altered thermal infrared emission spectrum is indicative of characteristics relating to molecular composition of the material.

15. An apparatus according to claim 14, wherein means for transiently generating a temperature differential includes means for applying energy to a surface region of the material adjacent to the infrared transparent portion of the transport system sufficient to cause transient heating in the thin surface layer portion of the material so as to enable transient thermal emission of infrared radiation from the thin surface layer portion.

16. An apparatus according to claim 14, wherein means for transiently generating a temperature differential includes means for applying energy to a surface region of the material adjacent to the infrared transparent portion of the transport system sufficient to cause transient cooling of the thin surface layer portion and superposition of the transmission spectrum of the cooled layer on the emission of infrared radiation from the lower portion of the material below the cooled layer and being at a higher temperature than the cooled layer.

17. An apparatus according to claim 14, wherein the means for detecting through the infrared transparent portion of the transport system includes means for detecting substantially only the transient altered thermal infrared emission spectrum which is substantially free of self-absorption by the material of emission infrared radiation.

18. An apparatus according to claim 14, wherein the means for applying energy to a surface region of the material includes means for applying one of heat and cold energy, one of pulsingly and continuously to the surface region of the material adjacent to the infrared transparent portion of the transport system.

19. An apparatus according to claim 18, wherein the means for applying energy to the surface region of the material includes one of applying energy directly to the surface region of the material and indirectly through the infrared transparent portion of the transport system, the infrared transparent portion being a thermally transparent portion enabling transmission of the applied energy therethrough.

20. An apparatus according to claim 14, wherein the material is one of a flowing material and a stationary material.

21. An apparatus according to claim 20, wherein the flowable material is one of a liquid, gas, powder, pellets, and a melt.

22. An apparatus according to claim 14, wherein the transport system includes at least one of a container and conduit for the flowable material and having the infrared transparent portion disposed as a window in a wall thereof, the means for detecting including a detector having a field of view of at least a portion of the window for detecting the transient altered thermal infrared emission spectrum of the material through the window.

23. An apparatus according to claim 22, wherein a portion of the window facing the flowable material with a convex surface for enabling contact with the flowable material.

24. An apparatus according to claim 22, wherein the material is a flowing material and is positioned in the wall of the transport system so that the moving material moves in parallel to an extent of the window.

25. An apparatus according to claim 22, wherein the material is a moving material and the window is positioned in the wall of the transport system so as to extend transversely to an initial moving direction of the moving material so that the moving material impinges on and is deflected from the window.

26. An apparatus according to claim 14, further comprising the means for determining characteristics relating to the molecular composition of the flowable material in accordance with the detected transient altered thermal emission.

* * * * *

UNITED STATES PATENT AND TRADEMARK OFFICE
CERTIFICATE OF CORRECTION

PATENT NO.    : 5,191,215
DATED         : March 2, 1993
INVENTOR(S)   : McClelland et al.

It is certified that error appears in the above-identified patent and that said Letters Patent is hereby corrected as shown below:

Column 1,
Line 4, after the Title and before CROSS REFERENCE TO RELATED APPLICATIONS, insert -- STATEMENT REGARDING FEDERALLY SPONSORED RESEARCH AND DEVELOPMENT
This invention was made in part with Government support under the United States Department of Energy Contract No. W-7405-Eng-82. The Government may have certain rights in this invention. --

Signed and Sealed this

Nineteenth Day of August, 2003

JAMES E. ROGAN
*Director of the United States Patent and Trademark Office*